United States Patent [19]

Vaez-Iravani

[11] Patent Number: 5,798,829
[45] Date of Patent: Aug. 25, 1998

[54] SINGLE LASER BRIGHT FIELD AND DARK FIELD SYSTEM FOR DETECTING ANOMALIES OF A SAMPLE

[75] Inventor: Mehdi Vaez-Iravani, Santa Clara, Calif.

[73] Assignee: Kla-Tencor Corporation, Milpitas, Calif.

[21] Appl. No.: 611,109

[22] Filed: Mar. 5, 1996

[51] Int. Cl.$^6$ ................................................. G01N 21/00
[52] U.S. Cl. ............................................ 356/237; 356/364
[58] Field of Search ........................ 356/237, 239, 356/394, 371, 364, 369, 338, 351, 358, 359, 360

[56] References Cited

U.S. PATENT DOCUMENTS

| | | | |
|---|---|---|---|
| 4,353,650 | 10/1982 | Sommargren | 356/360 |
| 4,449,818 | 5/1984 | Yamaguchi et al. | 356/237 |
| 4,595,289 | 6/1986 | Feldman et al. | 356/237 |
| 4,764,014 | 8/1988 | Makosch et al. | 356/356 |
| 4,871,257 | 10/1989 | Suzuki et al. | 356/237 |
| 5,037,202 | 8/1991 | Batchelder et al. | |
| 5,058,178 | 10/1991 | Ray | 356/237 |
| 5,379,150 | 1/1995 | Miyazaki et al. | 356/237 |
| 5,465,145 | 11/1995 | Nakashige et al. | |
| 5,469,259 | 11/1995 | Golby et al. | 356/359 |
| 5,606,418 | 2/1997 | Borden et al. | 356/364 |

FOREIGN PATENT DOCUMENTS

| | | |
|---|---|---|
| 0335163 | 10/1989 | European Pat. Off. |
| 61-198008 | 9/1986 | Japan |

OTHER PUBLICATIONS

"Wafer Inspection With a Laser Scanning Microscope," J. de la Rosa et al., AT&T Technical Journal, 65 (1986), Jan.–Feb., No. 1, Short Hills, NJ, U.S.A., pp. 68–77.

"Reticle Particle Detection System," T. Nishino et al., 8297 Hitachi Review 40(1991), Dec., No. 6, Tokyo, Japan, pp. 395–400.

"Linear Imaging in Scanning Polarisation/Interference Contrast Microscopy," by C.W. See and M. Vaez–Iravani, Electronics Letters, Sep. 25, 1986, vol. 22, No. 20, pp. 1079–1081.

"Linear and Differential Techniques in the Scanning Optical Microscope," by M. Vaez Iravani and C.W. See, Proc. SPIE, vol. 897, 43 (1988).

"Detection and Refractive Index Identification of Sub–micron Particles on Surfaces," by Taubenblatt and Batchelder, SPIE vol. 1821, 152, (1992).

"Measurement of the Size and Refractive Index of a Small Particle Using the Complex Forward–Scattered Electromagnetic Field," by Taubenblatt and Batchelder, Applied Optics, vol. 30, No. 33, Nov. 20, 1991.

"Phase Contrast and Amplitude Pseudoheterodyne Interference Near Field Scanning Optical Microscopy," by Vaez–Iravan and Toledo–Crow, Appl. Phys. Lett., vol. 62, No. 10, Mar. 8, 1993.

Primary Examiner—Hoa Q. Pham
Attorney, Agent, or Firm—Majestic, Parsons, Siebert & Hsue

[57] ABSTRACT

A single laser is used to provide light for both dark and bright field detection. The laser beam is split into two beams by a Wollaston prism and both beams are directed towards a sample to be inspected to illuminate two areas of the sample. The light reflected by or transmitted through the sample at the two spots is then combined by the same or a different Wollaston prism and the phase shift caused by any anomaly of a sample is detected as a phase shift between the two beams by a bright field detector. Light scattered by the sample at the two spots is detected by a dark field detector. A halfwave plate is used to orient the polarization plane of light from the laser incident on the Wollaston prism so that one of the two beams incident on the sample has a much higher intensity than the other and so that the sensitivity and the detection operation of dark field is not altered by the presence of two illuminated spots on the sample. A transparent dielectric at a suitable angle to the incident beam and the reflected or transmitted beam may be used to enhance bright field detection.

16 Claims, 4 Drawing Sheets

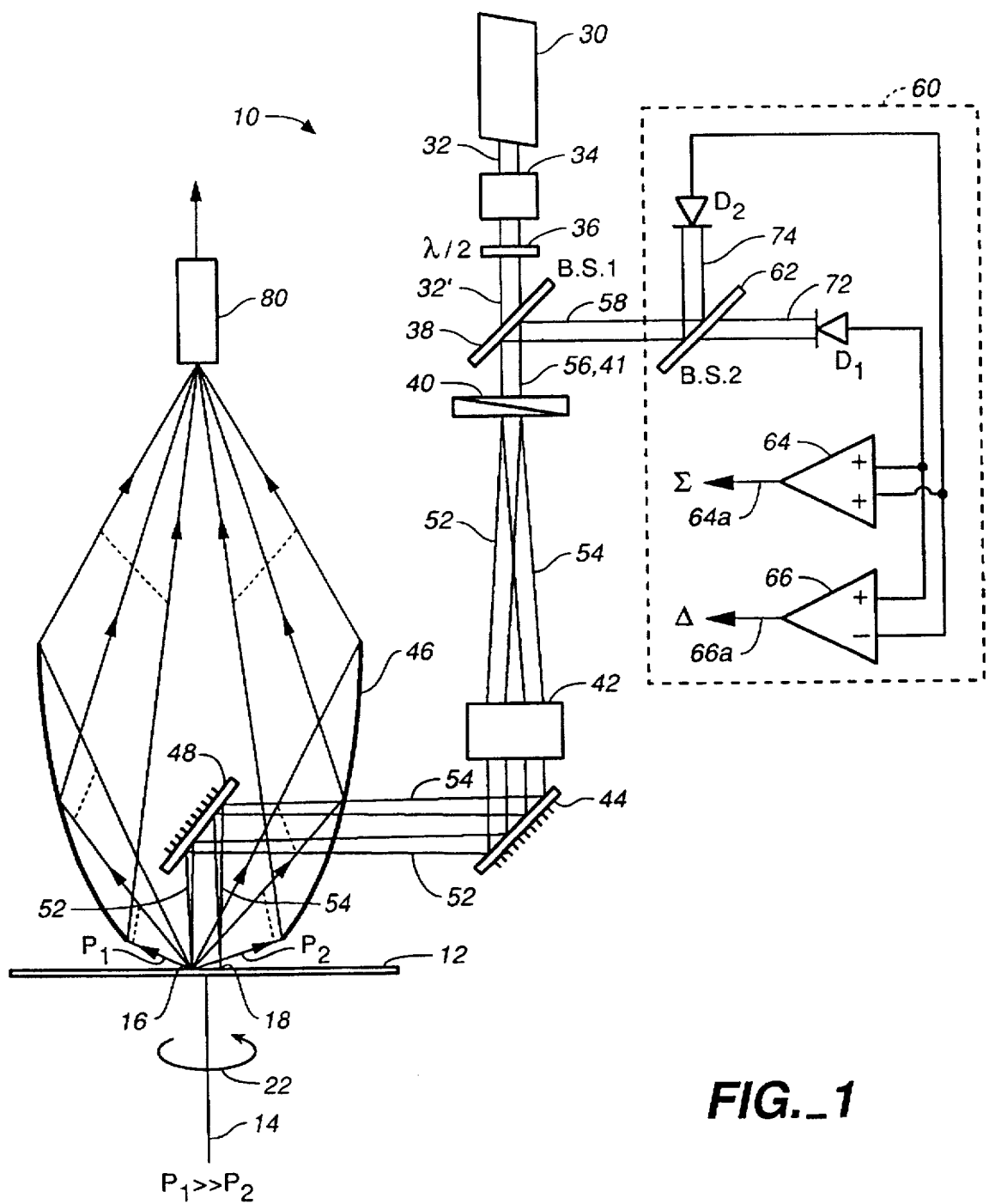
FIG._1

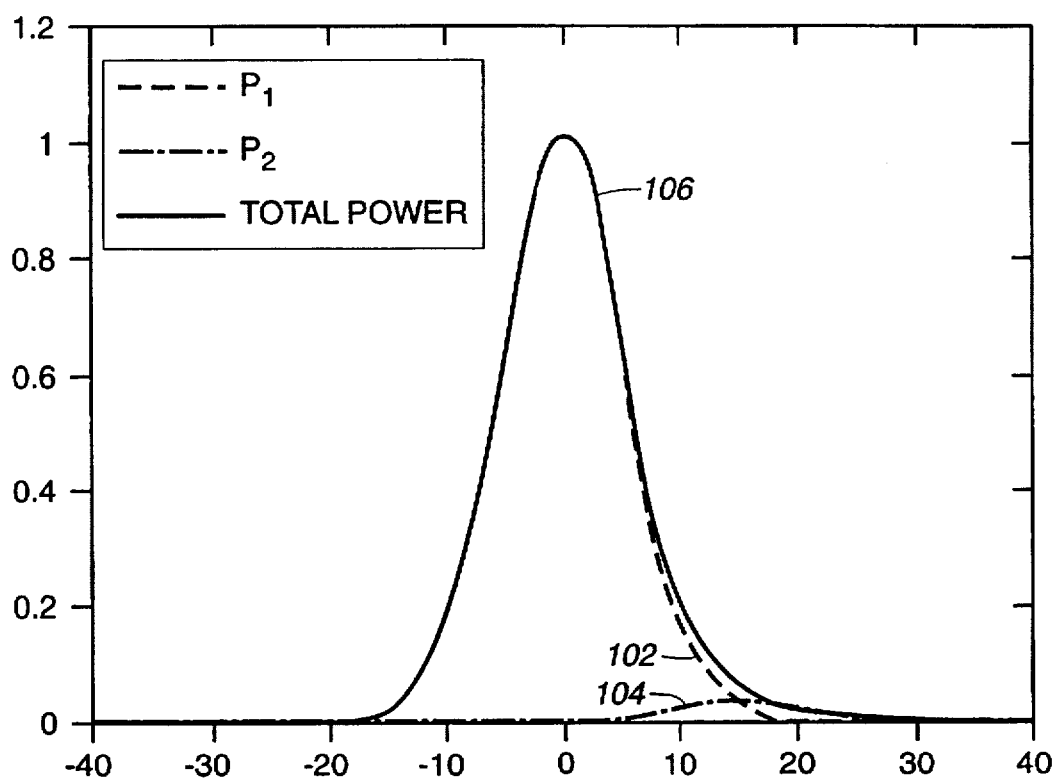
FIG._2

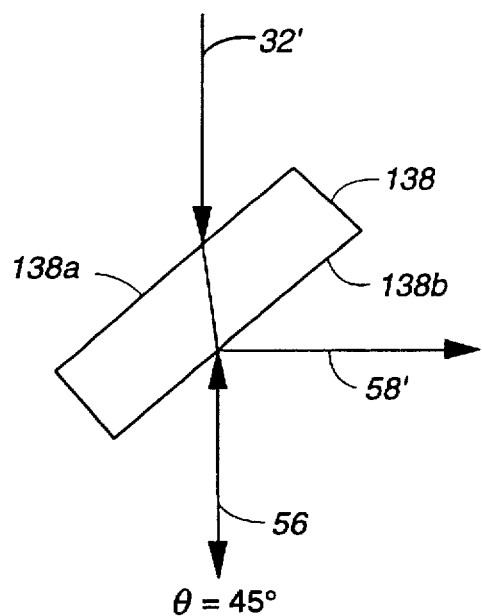
FIG._3A
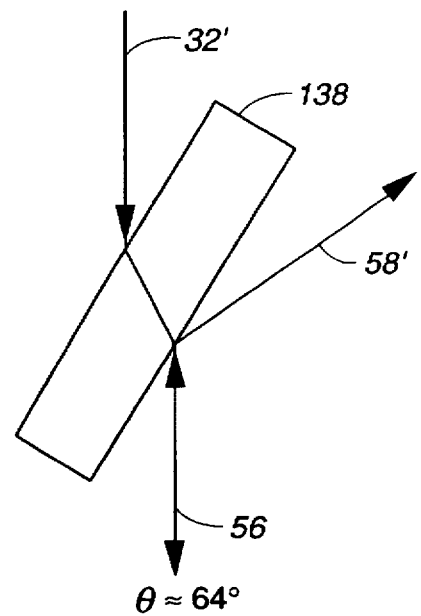
FIG._3B
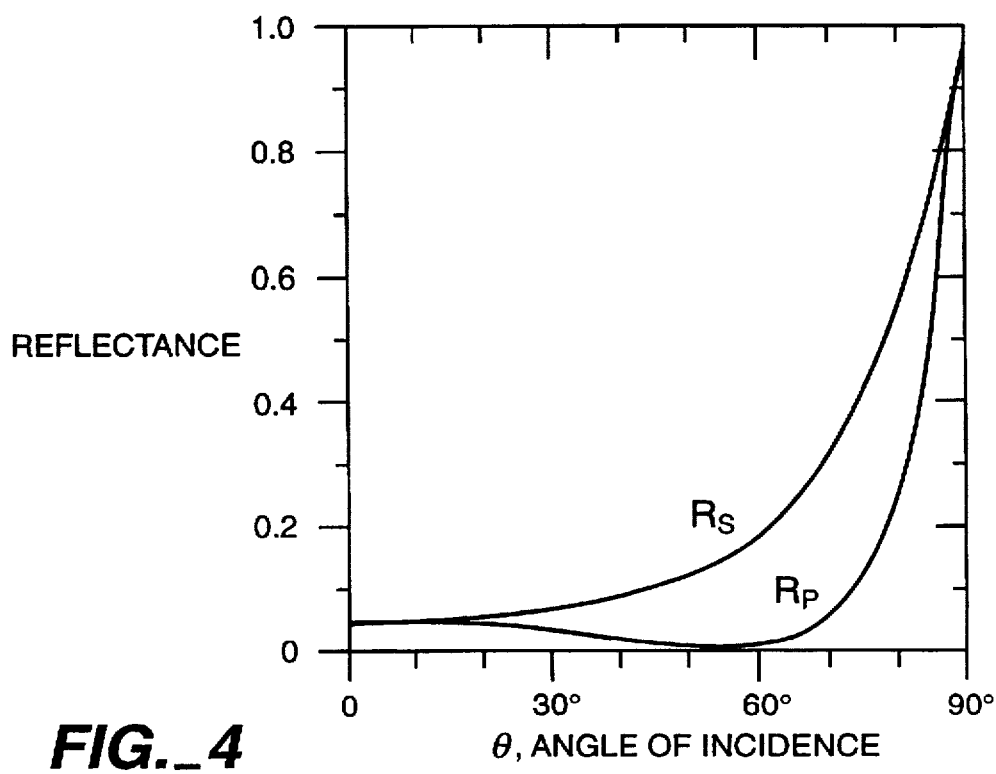
FIG._4

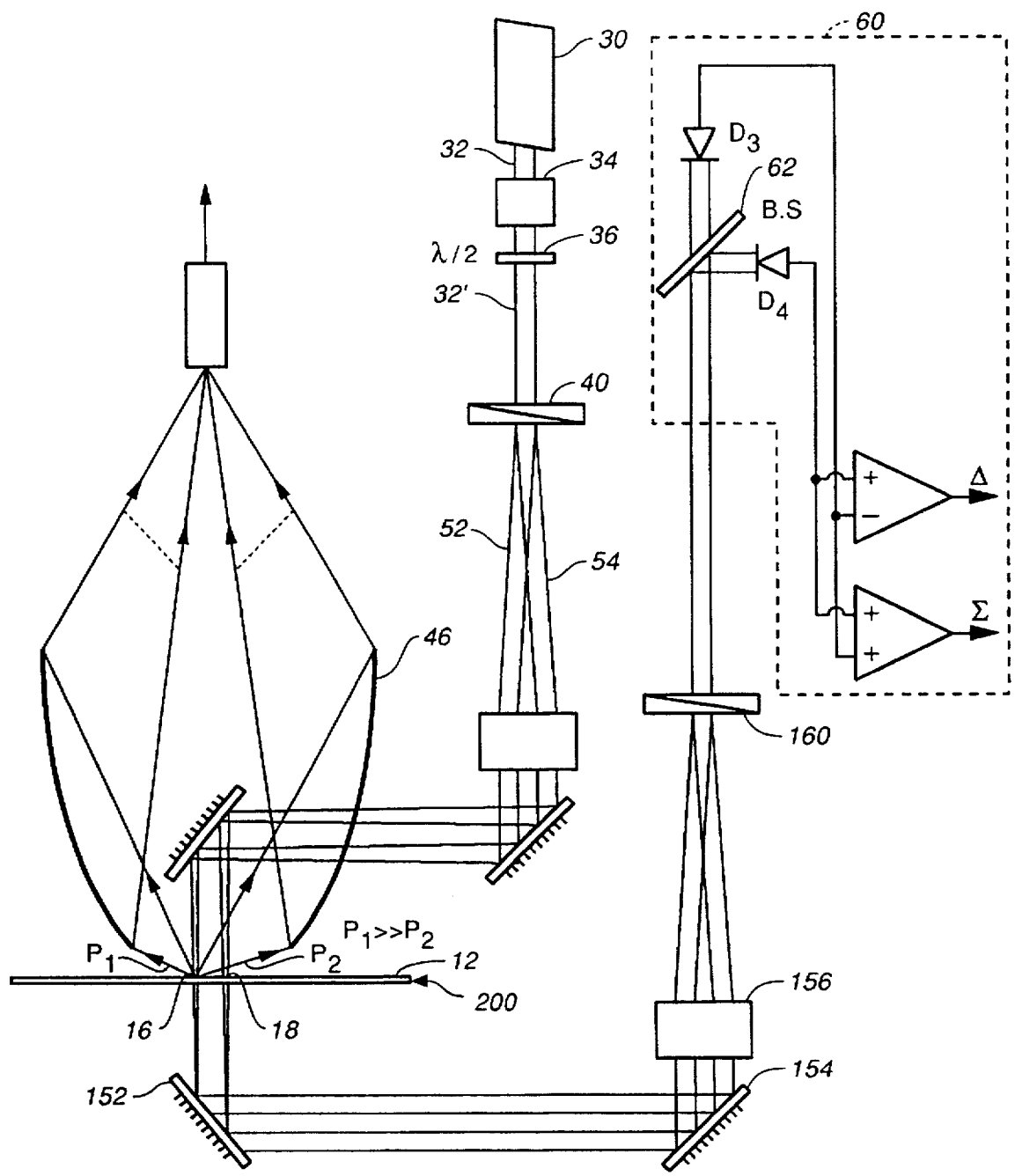
FIG._5

SINGLE LASER BRIGHT FIELD AND DARK FIELD SYSTEM FOR DETECTING ANOMALIES OF A SAMPLE

BACKGROUND OF THE INVENTION

This invention relates in general to systems for detecting anomalies of samples, and in particular to a single laser bright field and dark field system for detecting anomalies on samples such as semiconductor wafers, photomasks, reticles and ceramic tiles.

The size of semiconductor devices fabricated on silicon wafers has been continually reduced. At the present time, for example, semiconductor devices can be fabricated at a resolution of a half micron or less, and 64 megabit DRAMS are being fabricated with a 0.35 micron design rule. The shrinking of semiconductor devices to smaller and smaller sizes has imposed a much more stringent requirement on the sensitivity of wafer inspection instruments which are called upon to detect contaminant particles and surface defects that are small compared to the size of the semiconductor devices. In addition to the detection of the presence of a defect, frequently it is useful also to know the structural characteristics of the defect, such as whether a surface defect is an elevation or a depression in the surface.

Many wafer inspection instruments are dark field systems, where light scattered on a surface is inspected to detect particles and surface defects. One of the problems in a dark field system is that, due to the fact that information concerning structural characteristics of the defects may be lost because of the scattering, it may be difficult or impossible for dark field systems to determine the structural characteristics of the defects, such as whether the defect is an elevation or a depression in the surface. While it is possible for bright field systems to detect the structural characteristics of the defect, the ever present background signal can be many orders of magnitude larger than the feature related signal from the defect.

Thus none of the conventional systems or systems proposed is entirely satisfactory. It is therefore desirable to provide an improved anomaly detection system which can detect anomalies which are small relative to the size of the semiconductor devices as well as the structural characteristics of the defects.

SUMMARY OF THE INVENTION

This invention is based on the observation that both dark field detection and bright field detection may be employed for detecting particles and surface defects that are small compared to the size of semiconductor devices as well as the structural characteristics of the defects. While two lasers may be used, one for the bright field portion and one for the dark field portion of the system, it is advantageous to use a single laser for both portions of the system in a manner that facilitates the registration of areas detected by the two portions of the system.

One aspect of the invention is directed towards a system for detecting anomalies of a sample, comprising means for transmitting to said sample two substantially parallel optical incident beams. The beams are initially coherent but are of different polarizations, so that any anomaly of the sample and illuminated by one of the beams causes a phase shift in a beam resulting from transmission or reflection of said one of the incident beams by the sample. The system further comprises at least one dark field detector detecting light scattered by the sample from the two incident beams and a bright field detector detecting any phase shift in transmissions or reflections of the two incident beams by the sample.

Another aspect of the invention is directed towards a method for detecting anomalies of a sample, comprising the steps of transmitting to said sample two substantially parallel optical incident beams, said beams being initially coherent but of different polarizations, so that any anomaly of said sample and illuminated by one of the beams causes a phase shift in a beam resulting from transmission or reflection of said one of the incident beams by the sample; detecting light scattered by the sample from the two incident beams; and detecting any phase shift in transmissions or reflections of the two incident beams by the sample.

BRIEF DESCRIPTION OF THE DRAWINGS

FIG. 1 is a schematic diagram illustrating a combined dark field and bright field system for detecting anomalies on a surface to illustrate the preferred embodiment of the invention.

FIG. 2 is a graphical plot of the point spread function of the system of FIG. 1 to illustrate the preferred embodiment of the invention.

FIG. 3A is a schematic diagram illustrating the incident angle of the light of the system of FIG. 1 relative to a block of a transparent dielectric material useful for illustrating the invention.

FIG. 3B is a schematic diagram of the block of FIG. 3A, but where the incident angles of the laser light and its reflections relative to the block have been altered to improve the sensitivity of bright field detection to illustrate the preferred embodiment of the invention.

FIG. 4 is a graphical illustration of the reflectance of the block of transparent dielectric of FIG. 3B as a function of the angle of incidence to illustrate the preferred embodiment of the invention.

FIG. 5 is a schematic diagram illustrating a combined dark field and bright field system for detecting anomalies of a sample to illustrate an alternative embodiment of the invention.

For simplicity in description, identical components are identified by the same numerals in the application.

DETAILED DESCRIPTION OF THE PREFERRED EMBODIMENT

System 10 of FIG. 1 is a laser-based scanner anomaly detection system to illustrate the preferred embodiment of the invention. The illumination system and the light collection and detection system of FIG. 1 are stationary and the surface 12 of a sample to be inspected is moved along a spiral path. A spiral scan path is accomplished by rotating the surface about a shaft or axle by a rotary motor, and simultaneously translating the shaft or axle along a line using a linear translation stage and motor combination. The rotational motion of the surface about the shaft or axle, and the translational motion of the shaft or axle are coordinated by controlling the two motors so that the illuminated portion of the surface traces a spiral path on the substrate.

Surface 12 is a light reflective surface, such as that of a semiconductor wafer, photomask, reticle, ceramic tile, or other surface. As shown in FIG. 1, surface 12 to be inspected is rotated about a shaft or axle 14 located behind the plane of the paper, so that the illumination portion of the system 10 causes two spots 16 and 18 of surface 12 to be illuminated. Thus spots 16 and 18 are located on a tangential path of the rotational motion of surface 12 about axle or shaft 14. If surface 12 is rotated about axle 14 along the direction of arrow 22 indicated, then the portion of the surface first illuminated within spot 16 will be illuminated in spot 18 at a later time. Surface 12 is also moved relative to axle 14 in a translational motion so that spots 16, 18 will cover the entire surface 12 along a spiral path. Laser-based scanners employing the above-described rotational and translational motion of the surface with fixed illumination and collection systems are known and are described, for example, in U.S. Pat. Nos. 4,391,524; 4,526,468; and 4,598,997, all issued to Steigmeier, and in U.S. Pat. No. 5,377,001.

System 10 employs a bright field detection scheme that utilizes Nomarski's differential interference contrast principles. For a detailed explanation of Nomarski's differential interference contrast principles, please see "Quantitative Surface Topography Determination by Nomarski, Reflection Microscopy, I. Theory," by Delbert L. Lessor, John S. Hartman and Richard L. Gordon, *Journal of Optical Society of America* Vol. 69 No. 2, page 357 (1979). As shown in FIG. 1, laser 30 provides a coherent optical beam 32 substantially at a predetermined wavelength of linearly polarized light. Beam 32 is passed through a Faraday isolator 34 and a halfwave plate 36 and passes through a beam splitter 38 before it reaches a Wollaston prism 40. Beam splitter 38 is of a type that preferably transmits 85% or more of the light in beam 32 towards the Wollaston prism. Halfwave plate 32 is used to rotate the plane of polarization of beam 32 with respect to the vertical and horizontal axes of Wollaston prism 40 so that the beam 42 transmitted through beam splitter 38 is split into two beams 52 and 54, one with a vertical plane of polarization and the other with a horizontal plane of polarization. The beams 52 and 54 are passed through the beam forming optics 42, reflected by mirror 44 through an aperture in an ellipsoidal container 46 towards another mirror 48 which reflects the two beams towards surface 12 to illuminate the two spots 16, 18 described above. Where beams 52, 54 are substantially normal to surface 12, the specular reflections of the two beams 52, 54 by surface 12 substantially retrace the paths of the two incident beams, from surface 12 to mirror 48, mirror 44, beam forming optics 42, and are combined by Wollaston prism 40 into a single beam 56 again, with 85% or more of such combined beam passing through beam splitter 38 and then absorbed by Faraday isolator 34. But 15% or less of the light in such combined beam 56 is reflected by beam splitter 38 towards a bright field detector 60.

If A, B are the complex electric fields of the reflections of respective beams 52, 54 by surface 12 in the combined beam 56, then the complex fields A, B are given by the equations below:

$$A = e_1 r_1 \exp\{j(\omega t + \varnothing_1 \beta_1)\}$$

$$B = e_2 r_2 \exp\{j(\omega t + \varnothing_2 \beta_2)\}$$

where $e_1$, $e_2$ are the amplitudes of the incident electric fields of beams 52, 54 at spots 16, 18 respectively, and $r_1$ and $r_2$ are the reflectivities (including wafer reflectivities, and all other reflectivities encountered between the wafer and detector 60), $\omega$ is the angular optical frequency of laser 30 and $\varnothing_1$ and $\varnothing_2$ are the optical phases associated with or caused by surface 12 at spots 16, 18 respectively, and $\beta_1$ and $\beta_2$ are the average optical phases of two beams 52, 54 incident upon surface 12 and reflected therefrom, where the latter two terms $\beta_1$, $\beta_2$ also include the effect of microphonics in the system such as temperature and pressure fluctuations and mechanical vibrations. In a differential interference contrast system such as system 10, however, due to the proximity of the two beams 52, 54 to each other, these spurious effects are almost identical and can be ignored.

Polarizing beam splitter 62 has its axes oriented at approximately 45° with respect to the axes of the Wollaston prism, so that the transmitted beam 72 and the reflected beam 74 have complex electric fields $E_1$, $E_2$ given by the equations below:

$$E_1 = \frac{1}{\sqrt{2}} (A + B)$$

$$E_2 = \frac{1}{\sqrt{2}} (A - B)$$

Detector D1 detects the intensity $S_1$ of beam 72 and detector D2 detects the intensity $S_2$ of beam 74, where $S_1$, $S_2$ are proportional to quantities given below:

$$S_1 \alpha (E_1 \cdot E_1^*) \ \& \ S_2 \alpha (E_2 \cdot E_2^*)$$

$$S_1 \alpha \{I_1 + I_2 + 2\sqrt{I_1 I_2} \cos(\delta\phi + \beta)\} \text{ and}$$

$$S_2 \alpha \{I_1 + I_2 - 2\sqrt{I_1 I_2} \cos(\delta\phi + \beta)\} \text{ where}$$

$$I_1 = |e_1|^2; \ I_2 = |e_2|^2 \text{ and}$$

$$\delta\phi = \phi_2 - \phi_1 \ \& \ \beta = \beta_2 - \beta_1$$

In a manner known to those skilled in the art, the quantity $\beta$ can be adjusted by adjusting the lateral incident position of the beam for illuminating the surface on Wollaston prism 40; preferably, such relative position is adjusted so that $\beta$ has the value of 90° or $\pi/2$. The above equations for $S_1$ and $S_2$ therefore reduce to the following:

$$S_1 \alpha \{I_1 + I_2 - 2\sqrt{I_1 I_2} \sin(\delta\phi)\}$$

$$S_2 \alpha \{I_1 + I_2 + 2\sqrt{I_1 I_2} \sin(\delta\phi)\}$$

For small $\delta\phi$, $\sin(\delta\phi) \cong$ $$(\delta\phi) \rightarrow \text{linear response so that } S = (S_1 - S_2)\alpha\{4\sqrt{I_1 I_2} \ \delta\phi\}$$

For most anomalies, the phase difference $\delta\varnothing$ would be small, so that the above-described linearization process may be employed. Other schemes for linearizing the phase difference may also be used, such as that described in "Linear Imaging in Scanning Polarization/Interference Contrast Microscopy," by C. W. See and M. Vaez-Iravani, *Electronics Letters*, Sep. 25, 1986, Vol. 22, No. 20, pages 1079–1081.

Thus from the above equations, it is seen that the differential phase between the complex electric fields A, B of the reflections at spots 16, 18 is measured by the difference output 66a, and is given by the quantity S in the equations above. Thus system 10 can be calibrated to measure the differential phase between the complex electric fields A, B. One important feature of system 10 is the fact that, since the measured quantity S responds linearly to the differential phase between A, B, the measured quantity S preserves the sign of the differential phase; that is, whether the anomaly is a depression or an elevation on the surface 12. In this instance, a particle on the surface will give rise to a positive differential phase, just as with an elevation. An inherent feature of the Wollaston-based system 10 is that it allows arbitrary phase biasing between the two beams 52, 54, which results in a guaranteed linear response of the system. Furthermore, since the system is differential in nature, it has major advantages in terms of the rejection of common mode noise, and cancellation of vibrations which are along the beam direction affecting the light paths of the two beams. In a normal mode of operation, the phase difference is obtained at a high frequency. This allows the possibility of applying a high pass filter to the output differential phase signal which, in turn, greatly alleviates complications due to vibration induced lateral shift of the Wollaston prism and the light beams passing through the prism. The total reflectance signal at output 66a gives the total reflectance of a sample and can be used for normalizing the difference output signal at output 66a.

The ellipsoidal collector 46 reflects the scattered light from spots 16 and 18 towards a dark field detector 80. For a more detailed explanation of the operation of the ellipsoidal collector 46 and the dark field detector 80, please see U.S. patent application Ser. No. 08/216,834, filed Mar. 24, 1994, entitled "Process and Assembly for Non-destructive Testing of Surfaces," which is incorporated herein in its entirety by reference. Mirror 48 prevents specular reflection from spots 16 and 18 from reaching the dark field detector 80. For simplicity, only the light rays collected by collector 46 from spot 16 are shown in FIG. 1, it being understood that collector 46 will also collect light from spot 18 and direct such rays to detector 80. Also for clarity of illustration, the separation between the spots 16, 18 is exaggerated; such separation is typically half of a spot diameter or less.

While dark field detection can be very sensitive to small surface anomalies, dark field detection alone typically does not yield information on the structural characteristics of the surface anomaly. As noted above, the phase detection scheme described above for bright field detection can differentiate between depression on the one hand and elevation or particle on the other; such bright field detection can be used to supplement dark field detection to yield more information on the surface anomaly. If a first laser is used to illuminate a first spot on the surface 12 for dark field detection and a second laser is used to illuminated a second spot on the surface 12 for bright field detection, then in order to benefit from both dark and bright field detections, one must be able to identify or register the dark field data for a particular spot on the surface with the bright field data for the same spot. This is cumbersome and any misregistration errors would defeat the purpose of using both bright and dark field detection.

The scheme 10 of FIG. 1 avoids this problem altogether since a single laser is used so that both the bright field detector 60 and the dark field detector 80 are detecting from surface features on the same area or areas such as spots 16, 18 on surface 12. This eliminates any need for methodology to remedy misalignment of bright and dark field data.

To avoid reducing significantly the intensity of illumination and hence the detection sensitivity in dark field detection systems, the relative intensity of beams 52, 54 may be such that one (e.g. beam 52) is at a much higher intensity than the other, such as where one beam is at an intensity that is twenty times or more that of the other. The optical arrangement for achieving such ratio of intensities is explained below. As shown below, the above advantages of a single laser for both bright and dark field detection can be retained without sacrificing significantly the illumination and hence the detection sensitivity of dark field detection. This is illustrated in FIG. 2.

Many dark field detection systems have been designed assuming that only a single spot of the surface to be inspected is to be illuminated at any one time so that data processing is performed assuming the point spread function of a single spot. Therefore, the presence of two different spots 16, 18 may require a redesign of such systems to accommodate two different illuminated spots on surface 12, and is undesirable. The present invention eliminates the need for such redesign as explained below.

FIG. 2 is a graphical plot of the point spread function of the two illuminated spots 16, 18 as seen by detector 80 where the intensity of the beam with a first polarization and having power $P_1$ illuminating one spot is twenty-four times the intensity of the other beam with a second different polarization and power $P_2$ illuminating the other spot. As shown in FIG. 2, 102 is the point spread function of the spot illuminated by the beam with the first polarization and point spread function 104 is that of the spot illuminated by the beam with the other polarization. The sum of the two functions as seen by detector 80 is illustrated by curve 106. As is clear from FIG. 2, the combined point spread function of the two spots 16, 18 is essentially the same as that of the spot 16 illuminated by the beam with the first polarization alone. Hence the dark field detection system originally designed for detecting light scattered from a single illuminated spot need not be altered to accommodate a combined dark and bright field detection system such as system 10 of FIG. 1.

The halfwave plate 36 is used to rotate the plane of polarization of beam 32 so that the plane of polarization is at such angle to the vertical and horizontal axes of the Wollaston prism 40 that beam 52 of the first polarization has an intensity or power $P_1$ that is at least twenty times the intensity or power $P_2$ of the other beam 54.

The operation of the bright field detector 60 will now be described. Upon reflection by beam splitter 38, the portion of the beam 58 from reflection of beam 52 has P polarization and the portion of the beam 58 from the reflection of beam 54 has S polarization. Assuming that P is the total power of beam 56 before reflection by beam splitter 38, $P_p$ and $P_s$ are respectively the powers of the P polarization and S polarization portions of beam 56 and $\gamma$ is the ratio $P_p/P$, then the quantities P, $P_p$, $P_s$ are related as follows:

$$P_p = P\gamma \text{ and } P_s = P(1-y)$$

Then the intensity $I_{out}$ detected by detector D1 from beam 72 is proportional to quantity given as follows:

$$I_{out} \alpha \{P_p R_p + P_s R_s - 2\sqrt{P_p R_p P_s R_s} \sin\delta\phi\}$$

where $R_p$ is the reflectance of the beam splitter 38 with respect to light of P polarization and $R_s$ is the reflectance of beam splitter 38 with respect to light of S polarization. If the beam splitter 38 has equal reflectance for light of P and S polarizations and if $\gamma$ is 24/25, then the intensity detected by detector D1 is given approximately as follows:

$$I_{out} \alpha PR(1-2/58\emptyset)$$

where R is the reflectance of beam splitter 38 of light of both P and S polarizations.

In other words, if beam splitter 38 has the same reflectance irrespective of polarization, and where light of P polarization is of an intensity twenty-four times that of the S polarization, the phase shift that is detected by the bright field detector 60 is reduced only by about 60% despite the big difference (24 to 1) in intensity between the light of P polarization and the light of S polarization in beam 58. If beam splitter 38 transmits 85% of incident light and reflects 15% of the incident light, then the total power P of beam 58 is about 12% of the light provided by laser 30, where this percentage may be further reduced due to the imperfect light reflection at the surface 12.

One alternative scheme to the above described one is to orient the halfwave plate 36 so that beams 52 and 54 have equal intensities; this would increase the percentage of laser power delivered to the bright field detector 60 at the cost of reducing the intensity density of light delivered to the dark field detector and hence its sensitivity. Even so, the total power of beam 58 sent to the bright field detector 60 would only be 25% of that of the light provided by laser 30 (again not taking into account the further reduction in intensity due to the imperfect light reflection at the surface 12), and such power is only about twice that delivered using the scheme described above in reference to FIG. 2. In other words, at a modest reduction (by a factor of about 2) of the total power delivered to the bright field detector 60, the intensity or power for dark field detection is not noticeably reduced so that the detection sensitivity of the dark field portion of the system is preserved.

As noted above, where beams 52, 54 have the same intensity, this will require the data processing portion of the dark field detection system be altered to accommodate detection from two illuminated spots, which is undesirable. In other words, the scheme described above avoids a redesign of the dark field detection system at only a modest reduction in the total power of the light delivered to the bright field detector 60 and at a modest reduction of the phase shift signal detected by the detector 60.

The above-described 60% reduction in the phase shift signal can be compensated for by using a transparent dielectric material instead of a beam splitter 38 as described below in reference to FIGS. 3A, 3B and 4. As shown in FIG. 3A, instead of beam splitter 38, a block of a transparent dielectric material 138 is interposed between the halfwave plate 36 and the Wollaston prism 40. Block 138 has two substantially parallel surfaces 138a, 138b. Block 138 in FIG. 3A is oriented so that the surfaces 138a, 138b are at 45° to beams 32' and 56. FIG. 4 is a graphical illustration of the reflectance of glass at different incidence angles of an incident beam of light, showing the reflectances of the light of both P and S polarizations. As is evident from FIG. 4, if block 138 is made of glass, it has a higher reflectance of light of S polarization compared to that of P polarization except at very low and very high angles of incidence. At 45° angle of incidence as shown in FIG. 3A, the reflectance of light of S polarization is roughly an order of magnitude higher than that for light of P polarization. This will tend to compensate for the reduction in signal of the phase shift detected by detector 60. There is a range of angles around 45 degrees within which the relative reflectances of light of P and S polarizations will compensate for the reduction in signal of the phase shift detected by detector 60. Such range of angles have values that are smaller than the Brewster angle of glass as shown below. Thus if the incidence angle is chosen to be within such range, the reduction in the phase shift signal due to the disparity in intensities of beams 52, 54 is partially compensated for.

In reference to FIG. 4, the refractive index for glass is 1.5 so that the Brewster angle is about 56°. If a 64° incidence angle (greater than the Brewster angle) is chosen instead as illustrated in FIG. 3B, then the light reflectance of light of S polarization is about twenty to twenty-five times that of light of P polarization. In such event, the ratio $R_p/R_s$ is approximately equal to $(1-\gamma)/\gamma$, so that the intensity detected by detector D1 is proportional to a quantity given as follows:

$$I_{out} \alpha P\{|R_p\gamma + (1-\gamma)R_s| - 2\sqrt{(R_pR_s)\gamma(1-\gamma)} \ \sin\delta\phi\}$$

-continued $$\therefore I_{out}\alpha PR_s \left\{ \left[ \gamma\left(\frac{R_p}{R_s}\right) + (1-\gamma) \right] - 2\sqrt{\left(\frac{R_p}{R_s}\right)\gamma(1-\gamma)} \ \sin\delta\phi \right\}$$

$$I_{out}\alpha PR_s(1-\gamma)\{1-\sin(\delta\phi)\}$$

In other words, by using a transparent dielectric having a reflectance ratio $R_p/R_s$ that compensates for the big difference in intensity between the beams 52, 54, the above-described reduction in the phase shift signal detected by detector 60 is entirely compensated for, so that there is no longer such reduction. Again there is a range of angles around 64 degrees within which the relative reflectances of light of P and S polarizations will compensate for the reduction in signal of the phase shift detected by detector 60. In general, to compensate for the reduction in the phase shift signal, the value of the incidence angle may be chosen from two ranges of values, with the values within one range less than and with values within the other range greater than the Brewster angle.

From the equations above, the fringe visibility of detection 60 can be derived and is given by the expression on the left hand side of the equation below. For best results, the fringe visibility of detection 60 should be as high as possible, that is, as close to 1 as possible. For a practical system, it is assumed that the fringe visibility of detection 60 is greater than 0.9, as given by the equation below:

$$\frac{2\sqrt{\frac{R_s}{R_p}}\sqrt{\frac{P_r}{P_s}}}{\left(\frac{R_s}{R_p}\right)+\left(\frac{P_p}{P_s}\right)} \geq 0.9$$

where $$\frac{R_s}{R_p} = \left[\frac{\cos(\theta-\theta^1)}{\cos(\theta+\theta^1)}\right]^2$$

with $\theta$=angle of incidence
$\theta'$=angle of refraction=$\sin^{-1}[(1/n)\sin(\theta)]$
n=refraction index of beam-splitter material.

Note that if other values of fringe visibility are acceptable, then one simply changes 0.9 to one of those values.

Preferably, the choice of angle of incidence such as illustrated in FIGS. 3A, 3B is such that fringe visibility is optimized. Once a suitable material has been selected for the transparent dielectric in block 138 so that its refractive index is known, then the above equations for the fringe visibility may be used to derive an optimum value for the incident angle between beams 32', 56 and the two surfaces 138a, 138b of block 138.

While the invention has been described above by reference to detection of light reflected from an opaque surface 12 such as that of a semiconductor wafer, a slightly modified scheme may be used for detecting anomalies on surfaces of or within layers of material that are transparent. This is illustrated in FIG. 5. As shown in FIG. 5, the light transmitted towards spots 16, 18 on surface 12 of a layer of transparent material 200 will pass through the surface and layer and be reflected by reflectors 152, 154 towards beam forming optics 156 and combined by a second Wollaston prism 160 (designed to be complementary with the first Wollaston prism 40) and directed to detector 60 to be detected in the same manner as described above. Since no reflected light will retrace the path of the incident beam towards the laser. no beam splitter will be necessary in the light path between laser 30 and surface 12.

While the invention has been described above by reference to various embodiments. it will be understood that different changes and modifications may be made without departing from the scope of the invention which is to be limited only by the appended claims.

What is claimed is:

1. A system for detecting anomalies of a sample. comprising:

means for transmitting to said sample two substantially parallel optical incident beams. said beams being initially coherent but of different polarizations. so that portions of the beams are reflected or transmitted by the sample;

at least one dark field detector detecting intensity of light scattered by the sample from the two incident beams; and a bright field detector detecting any phase shift between the reflected or transmitted portions of the two incident beams.

2. The system of claim 1, further comprising means for combining the reflected or transmitted portions of the two beams to form a combined beam; wherein said bright field detector includes:

means for separating the combined beam or a beam obtained therefrom into a first and a second output beam having different polarizations; and means for detecting the first and second output beams to provide two outputs and for subtracting the two outputs to provide a phase shift signal.

3. The system of claim 1, wherein one of the two incident beams is at a higher intensity than the other of the two incident beams.

4. The system of claim 3, wherein one of the two incident beams is at an intensity at least 20 times that of the other of the two incident beams.

5. The system of claim 1, said transmitting means including:

a laser to provide a coherent light beam towards the sample;

a beam splitter passing the coherent light beam from the laser towards the sample. and reflecting reflections by the sample of such beam towards the bright field detector. wherein the beam splitter passes 85% or more of the light incident on it.

6. The system of claim 1, said transmitting means including a body of a transparent dielectric material.

7. The system of claim 6, wherein said transmitting means includes means for providing a laser beam. said dielectric material having a Brewster angle. said body being in the shape of a block with an incident surface and a reflecting surface. said two surfaces substantially parallel to one another. said beam provided by the laser being directed towards the incident surface at an incident angle which has a value in one of two ranges. the values of one of said two ranges being greater than and the values of the other of said two ranges being smaller than the Brewster angle of the dielectric material.

8. The system of claim 1. said two incident beams simultaneously illuminating at least two areas of the sample. wherein the at least one dark field detector detects light scattered by the simultaneously illuminated areas of the sample and the bright field detector detects the reflected or transmitted portions of the two beams from the simultaneously illuminated areas of the sample.

9. A method for detecting anomalies of a sample. comprising the steps of transmitting to said sample two substantially parallel optical incident beams. said beams being initially coherent but of different polarizations. so that portions of the beams are reflected or transmitted by the sample;

detecting light scattered by the sample from the two incident beams without substantially detecting light directly from the incident beams and the reflected or transmitted portions; and detecting any phase shift between the reflected or transmitted portions of the two incident beams.

10. The method of claim 9, further comprising combining the reflected or transmitted portions of the two beams by the sample to form a combined beam; wherein said phase shift detecting step includes:

separating the combined beam or a beam obtained therefrom into a first and a second output beam having different polarizations; and detecting the first and second output beams to provide two outputs and for subtracting the two outputs to provide a phase shift signal.

11. The method of claim 9, wherein one of the two incident beams is at a higher intensity than the other of the two incident beams.

12. The method of claim 11, wherein one of the two incident beams is at an intensity at least 20 times that of the other of the two incident beams.

13. The method of claim 9, said transmitting step including:

directing a coherent light beam towards the sample;

providing a beam splitter passing the coherent beam from the laser towards the sample. and reflecting reflections from the sample of such beam towards the bright field detector, wherein the beam splitter passes 85% or more of the light incident on it.

14. The method of claim 13, wherein said transmitting step includes providing a body of a transparent dielectric material for passing the coherent beam towards the sample and reflecting reflections by the sample towards a bright field detector, said body being in the shape of a block with an incident surface and a reflecting surface. said two surfaces being substantially parallel to one another. said transmitting step including directing the coherent beam towards the incident surface at an incident angle.

15. The method of claim 14, further comprising the step of determining, prior to the directing step, an optimal value for the incident angle as a function of the index of refraction of the dielectric material, and of a desired fringe visibility.

16. The method of claim 9, said transmitting step causing the two incident beams to simultaneously illuminate at least two areas of the sample, wherein the two detecting steps detect light scattered by and phase shift between the transmitted portions or reflected portions from the simultaneously illuminated areas of the sample.

* * * * *